US008795193B2

(12) United States Patent
Zeng et al.

(10) Patent No.: US 8,795,193 B2
(45) Date of Patent: *Aug. 5, 2014

(54) DEVICES AND METHODS FOR SUPPRESSION OF TINNITUS

(71) Applicant: The Regents of the University of California, Oakland, CA (US)

(72) Inventors: Fan-Gang Zeng, Irvine, CA (US); Qing Tang, Irvine, CA (US); Jeffrey Alan Carroll, Rancho Santa Margarita, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/745,213

(22) Filed: Jan. 18, 2013

(65) Prior Publication Data
US 2013/0204170 A1 Aug. 8, 2013

Related U.S. Application Data

(63) Continuation of application No. 12/746,171, filed as application No. PCT/US2008/085652 on Dec. 5, 2008, now Pat. No. 8,357,102.

(60) Provisional application No. 60/992,638, filed on Dec. 5, 2007.

(51) Int. Cl.
*A61B 5/12* (2006.01)
(52) U.S. Cl.
CPC ................................. *A61B 5/128* (2013.01)
USPC ........................................................ 600/559

(58) Field of Classification Search
USPC ............................................ 607/55; 600/559
See application file for complete search history.

(56) References Cited

U.S. PATENT DOCUMENTS

| | | | |
|---|---|---|---|
| 5,795,287 A | 8/1998 | Ball et al. |
| 6,047,074 A | 4/2000 | Zoels |
| 6,155,971 A | 12/2000 | Calhoun |
| 6,377,693 B1 | 4/2002 | Lippa |
| 6,394,969 B1 | 5/2002 | Lenhardt |
| 6,671,559 B2 | 12/2003 | Goldsmith |
| 7,613,519 B2 | 11/2009 | De Ridder |
| 7,734,340 B2 | 6/2010 | De Ridder |
| 7,854,697 B2 | 12/2010 | Davis |
| 8,353,846 B2 | 1/2013 | Henry et al. |
| 2001/0051776 A1 | 12/2001 | Lenhardt |
| 2002/0091423 A1 | 7/2002 | Rubinstein et al. |
| 2002/0173697 A1 | 11/2002 | Lenhardt |

(Continued)

OTHER PUBLICATIONS

Supplementary European Search Report, EP Appl. No. 08858980.9, 6 pages (Dec. 21, 2012).

*Primary Examiner* — Allen Porter, Jr.
(74) *Attorney, Agent, or Firm* — Cooley LLP

(57) ABSTRACT

Methods and devices for treating tinnitus in human or animal subjects wherein the subject is caused to perceive a tinnitus suppressing sound which fully or partially suppresses the subject's tinnitus. In some embodiments of this method, the subject selects a sound that he or she perceives to be the same as the tinnitus and that sound (or a similar sound that is complementary to the subject's perceived tinnitus) is then used as the tinnitus suppressing sound. In other embodiments, the tinnitus suppressing may be a sound that has previously been determined to suppress tinnitus in a substantial number of subjects.

24 Claims, 7 Drawing Sheets

(56) References Cited

U.S. PATENT DOCUMENTS

| | | |
|---|---|---|
| 2002/0177877 A1 | 11/2002 | Choy |
| 2004/0059251 A1 | 3/2004 | Choy |
| 2004/0141624 A1 | 7/2004 | Davis et al. |
| 2005/0043646 A1* | 2/2005 | Viirre et al. ............ 600/545 |
| 2005/0113871 A1 | 5/2005 | Choy |
| 2006/0095090 A1* | 5/2006 | De Ridder ............ 607/57 |
| 2007/0021804 A1 | 1/2007 | Maltan et al. |
| 2009/0018466 A1 | 1/2009 | Materna |
| 2009/0028352 A1 | 1/2009 | Petroff |
| 2009/0124850 A1 | 5/2009 | Moore |
| 2009/0270673 A1 | 10/2009 | Abolfathi |
| 2010/0121411 A1 | 5/2010 | Hochmair |

\* cited by examiner

DEVICES AND METHODS FOR SUPPRESSION OF TINNITUS

RELATED APPLICATIONS

This application is a continuation of U.S. patent application Ser. No. 12/746,171, filed on Jan. 20, 2011, now U.S. Pat. No. 8,357,102, which is a National Stage Entry of PCT Application No. PCT/US08/85652 filed Dec. 5, 2008, and also claims priority to U.S. Provisional Patent Application No. 60/992,638 filed Dec. 5, 2007, the entire disclosure disclosures of which is are expressly incorporated herein by reference.

STATEMENT REGARDING GOVERNMENT SUPPORT

This invention was made with Government support under Grant No. DC-002267, awarded by the National Institutes of Health. The Government has certain may have rights in this invention.

FIELD OF THE INVENTION

The present invention relates generally to biomedical devices and methods and more particularly to devices and methods usable for the treatment of tinnitus.

BACKGROUND OF THE INVENTION

Tinnitus is the perception of sound in the absence of corresponding external sounds. Tinnitus may be caused by injury, infection or the repeated bombast of loud sound, and can appear in one or both ears. Although known for its high-pitched ringing, tinnitus is an internal noise that varies in its pitch and frequency. The sound perceived may range from a quiet background noise to a signal loud enough to drown out all outside sounds.

Tinnitus affects approximately 50 million Americans or about 15% of the general population. There is no effective treatment to ameliorate tinnitus. The prior art has included devices and methods that attempt to mask tinnitus.

General Hearing and several others manufacture an earpiece that can generate sound. The masking methods work well for people who suffer mild forms of tinnitus but don't work for people who suffer from loud tinnitus because to mask the tinnitus, the external sound has to be louder than the tinnitus.

Some treatments, such as drugs, surgery, psychotherapy and masking, exist, but none are consistently effective and may have significant side effects. Here we propose to use sound to suppress tinnitus. Different from previous masking methods, which use an external sound that is typically louder than the tinnitus and has similar pitch quality to the tinnitus, we propose to use optimized sounds that may be softer and have different pitch qualities than the tinnitus. Another significant difference between previous masking devices and the present suppressing method is that the masking effect is instantaneous, while the present suppressing method usually takes time to develop and decay. The sound can be delivered either acoustically via an audio device (e.g., MP3 players, iPod® devices, or other ear devices) or electrically via a temporary or permanent implant.

In particular, various medications have been used to treat tinnitus, which are aimed at the disease or its co-morbidities. Tinnitus is often associated with anxiety and depression. Whether the condition causes psychological distress or whether tinnitus is more prevalent in people with psychological disorders is under debate. It has been suggested that tricyclic antidepressants treat the underlying psychological problems rather than the tinnitus directly. Some studies have demonstrated significant decrease in tinnitus intensity with the administration of intravenous (IV) lidocaine but have not reproduced the effect with oral analogues such as tocainide. IV administration of lidocaine is not a practical method due to its short half-life and serious side effects. Other agents, such as carbamazepine, alprazolam, baclofen, betahistine, and cinnarizine have also been studied as possible tinnitus treatments, with inconsistent results. Selective serotonin reuptake inhibitors have shown no benefit or a slight benefit in placebo-controlled studies.

Tinnitus masking devices of the prior art deliver a continuous low-level noise or tone to the ear that results in camouflaging of the tinnitus. Use of the device has been shown to reduce tinnitus severity. The Neuromonics tinnitus treatment is a new method of acoustic stimulation in combination with a structured program of counselling. The device output is a broadband stimulus that is constructed for each individual's hearing profile. Three clinical trials reported general improvement in quality of life of patients using this treatment. Hearing aids also grant partial or total relief from tinnitus by amplifying external sound stimuli thereby decreasing the awareness of the presence of tinnitus. Hearing aids are usually tried as first line treatment in patients with tinnitus in the presence of hearing loss. Hearing aids can also be used in combination with sound generators that increase the rate of success.

In the end of 1980s the neurophysiological model of tinnitus was proposed which then elicited the development of a new therapeutic approach called tinnitus retraining therapy (TRT). TRT consists of counselling along with delivery of a low-level, constant white noise to the affected ear(s) of a patient. The sound usually results in habituation of the patient's auditory system to the tinnitus thereby decreasing the patient's awareness of their condition. The rate of success varies between different patients. TRT requires one-to-two years of therapy for effective management of tinnitus.

Cochlear implantation has been found to be effective in reducing tinnitus in 28% to 79% of patients who have associated bilateral severe sensorineural hearing loss in previous studies. Exacerbation of tinnitus is reported in 9% of patients after cochlear implantation. Success with cochlear implants in decreasing tinnitus has led to other forms of electric stimulation, including transtympanic stimulation of the cochlea, vestibulocochlear nerve stimulation, and transcranial magnetic stimulation of the auditory cortex. Recent studies have shown that 1 out of 3 cochlear implant users and 5 out of 11 (45%) transtympanic subjects showed substantial or total tinnitus relief while stimulated by high rate pulse trains. More than that, the external perception was either presented subthreshold or diminished to below threshold within a short period of time. This is the ideal situation for tinnitus suffers since both the tinnitus and external stimulus are not perceived as a result. In a review of the literature, unilateral cochlear implant use was suggested to be associated with decline of contralateral tinnitus in 67% of patients. The effect of a cochlear implant is demonstrated to be due to masking of tinnitus by surrounding sounds that are newly perceived or from electrical stimulation of the auditory nerve. The mechanisms underlying the complexity of tinnitus are unclear, and a cure for this condition remains elusive. The prevailing theories generally point to either a central or peripheral source of subjective tinnitus, defined as sound perceivable only to the patient without a clear organic cause. The reality most likely involves a combination of both, with peripheral injuries and pathology causing functional and architectural changes in the central nervous system.

United States Patent Application Publication 2007/0203536 (Hochmair et al.) describes cochlear implant devices as well as other implantable devices usable to deliver tinnitus treatment. The entire disclosure of United States Patent Application Publication 2007/0203536 is expressly incorporated herein by reference.

U.S. Pat. No. 7,347,827 (Choy) describes monofrequency tinnitus patient treatment apparatus and process wherein phase cancellation effects are purported to be achieved by utilizing an externally generated sound which is subjectively selected by the monofrequency tinnitus patient to match in both tone and loudness his or her tinnitus sound. This subjectively selected externally generated sound wave which matches in tone and loudness the patient's tinnitus sound, is either (i) sequentially phase shifted through a plurality of phase shift sequence steps totaling at least 180 degrees or (ii) alternatively is directly phase shifted in essentially a single step motion into a 180 degree, out-of-phase reciprocal, canceling relationship with the patient determined tinnitus tone. The sequential steps of the phase shifted tone or the directly phase shifted tone are applied to the tinnitus patient to effect cancellation or diminishment of the patient's tinnitus. The entire disclosure of U.S. Pat. No. 7,347,827 (Choy) is expressly incorporated herein by reference.

Phase cancellation techniques, such as that described in U.S. Pat. No. 7,347,827 (Choy) may not be optimally effective in treating tinnitus. Most tinnitus is of high frequency (>1000 Hz) although some low-frequency tinnitus cases do exist. However, even if a person's tinnitus is low frequency, the phase canceling techniques may be ineffective or less than optimal because the perceived tinnitus sound is a neural impulse not an acoustic sound and cannot be physically or externally cancelled by phase inversion. Physiologically all sounds will be half-wave rectified in the cochlea and become digital-like pulses (called action potentials) in the nervous system. An out-of-phase external sound will add, rather than cancel, the internally-generated tinnitus.

Tinnitus occurs in the setting of sensorineural hearing loss in the majority of patients, thus the postulate that tinnitus originates peripherally in the cochlea. Noise damage causes molecular changes to structural proteins in stereocilia and the cuticular plate. Cytoplasmic calcium levels increase dramatically in response to sound, potentially disrupting normal hair cell function. Progressive insult results in complete destruction of hair cells in certain regions of the basilar membrane. Aberrant auditory signals occur around areas of hair cell loss, an edge effect that results in the perception of sound. Furthermore, auditory nerve fibers are spontaneously active during quiet, resulting in neurotransmitter release. Loss of the spontaneous activity can lead to abnormal central auditory activity, which could be perceived as sound. Lack of sound input and edge effects as a cause of tinnitus could explain the reduction of tinnitus commonly seen following cochlear implantation. Tinnitus suppression by electrical stimulation in hearing and deaf patients has been shown in a relatively recent study.

On the other hand, not all patients with hearing loss experience tinnitus, and not all tinnitus patients have hearing loss. Sectioning of the auditory nerve can result in tinnitus, suggesting a central etiology. Positron emission tomography (PET) imaging of patients with tinnitus shows unilateral neural activity in Brodmann areas 21,22, and possibly 42. These effects were decreased with lidocaine administration, a known suppressor of tinnitus. Sounds caused bilateral activity regardless of which ear was stimulated. Patients who experienced tinnitus in response to facial movement showed unilateral changes in cerebral blood flow. Another study using single photon emission computed tomography (SPECT) imaging during tinnitus showed a 16% increase in signal in the right auditory cortex and a 5% increase in the left, whereas noise caused bilateral change. The effect was eliminated by lidocaine administration. This difference in the activation pattern supports a theory of central generation of tinnitus.

This interpretation is consistent with animal models of tinnitus showing changes in spontaneous activity of the dorsal cochlear nucleus (DCN) following noise or cisplatin exposure. This hyperactivity persists following ablation of the damaged cochlea, suggesting that while a peripheral injury may stimulate a change in the DCN, the central hyperactivity is independent of peripheral input.

Tinnitus has been separated in three categories depending on severity and if hearing loss is present. Category 0 is characterized by the tinnitus having a low impact on the person's life. Categories 1 and 2 are used to describe tinnitus with a high impact on life with Category 2 indicating the presence of subjective hearing loss that accompanies the tinnitus. For our studies this convention was followed but a second parameter based on loudness was defined. The loudness parameter was determined by each subject as Low, Moderate or High. On a 10-point scale with 1 being the lowest sound (threshold) and 10 being the upper limit of loudness, Low is 0 to 3, Moderate is 3 to 6, and High is 6 to 10. Careful measures were taken to ensure each subject understands they are ranking loudness and not annoyance.

FIG. 1 of this patent application is a graphic representation of tinnitus severity classification and the typical tinnitus patient population. Patients within category 0 are least likely to seek tinnitus treatment. Category 1 and 2 patients with low levels of loudness are likely to be helped by TRT. It has been shown that TRT helps in relaxation for a majority of patients (72.5%) but benefits a much smaller percentage with respect to their ability to work (25.5%) and sleep (47%). At present, category 1 and 2 patients with high levels of loudness are often left without effective treatment.

There remains a need in the art for the development of new devices and methods for the treatment of tinnitus.

SUMMARY OF THE INVENTION

The present invention provides methods and devices for suppressing tinnitus rather than merely masking it.

In accordance with one aspect of the present invention, there is provided a method for treating tinnitus in a human or animal subject comprising the step of causing the subject to perceive a tinnitus suppressing sound which fully or partially suppresses the subject's tinnitus. In some embodiments of this method, the subject selects a sound that he or she perceives to be the same as the tinnitus and that sound (or a similar sound that is complementary to the subject's perceived tinnitus) is then used as the tinnitus suppressing sound. In other embodiments of this method, the tinnitus suppressing may be a sound that has previously been determined to suppress tinnitus in a substantial number of subjects. In some embodiments of this method, the tinnitus suppressing sound is perceived by the subject as being softer than the tinnitus, thereby lowering the subject's perceived sound environment. In some embodiments of this method, at least one variable of the tinnitus suppressing sound is varied to optimize the degree to which the subject's tinnitus is suppressed. The tinnitus suppressing sound may be delivered as acoustic sound or as electrical stimulus, such as electrical stimuli delivered via a cochlear implant.

Further in accordance with the present invention, there is provided a device for suppressing tinnitus in a human or animal subject, such device comprising an apparatus which causes the subject to perceive a tinnitus suppressing sound that results in suppression of the subject's tinnitus. In some embodiments of this device, the device may comprise apparatus that enables the subject to hear a number of sounds and to select a particular sound that he or she perceives to be the same as the tinnitus and the device may thereafter play the selected sound or another sound that is complementary to the selected sound as the tinnitus suppressing sound. In other embodiments of this device, the tinnitus suppressing sound may be a sound that has previously been determined to suppress tinnitus in a substantial number of subjects. In some embodiments of this device, the tinnitus suppressing sound will be played such that it is perceived by the subject as being softer than the tinnitus, thereby lowering the subject's perceived sound environment. In some embodiments of this device, at least one variable of the tinnitus suppressing sound may be varied to optimize the degree to which the subject's tinnitus is suppressed. This may be accomplished using a biofeedback processor or other suitable apparatus. The device may deliver the tinnitus suppressing sound may be delivered as acoustic sound (e.g., a sound playing device and speaker(s) or earpiece(s)) or as electrical stimulus (e.g., an electrical signal generating or delivering device which delivers the signal to the subject by way of an inserted or implanted electrode, electrode array or cochlear implant).

Further aspects, details, objects, elements, steps and advantages of the present invention will be understood by those of skill in the art upon reading of the detailed description and examples set forth below.

DETAILED DESCRIPTION AND EXAMPLES

The following detailed description and the accompanying drawings to which it refers are intended to describe some, but not necessarily all, examples or embodiments of the invention. The described embodiments are to be considered in all respects only as illustrative and not restrictive. The contents of this detailed description and the accompanying drawings do not limit the scope of the invention in any way.

When tinnitus is masked, as in the prior art, the tinnitus sound is covered with a masking sound, such as a white noise or band passed noise, that is equal to or greater in volume than the tinnitus sound. Thus, when tinnitus is masked, the subject's sound environment is the same or louder than listening to their tinnitus alone since the masking sound must be at least equal in volume to the tinnitus sound in order to completely cover the tinnitus sound. If the masker is presented quieter than the tinnitus, a case known as partial masking occurs. As the name indicates, this is when the tinnitus is partially covered so it appears lower in volume but the presence of the partial masker makes the total sound environment approximately the same. The present invention suppresses tinnitus by providing to the subject a tinnitus suppression sound (which may be an external acoustic sound or electrical cochlear or neural stimulation that corresponds to the desired tinnitus suppression sound). The tinnitus suppression sound may be lower in volume than the tinnitus and will substantially or completely eliminate the subject's perception of the tinnitus. As a result, the subject hears only the lower volume suppression sound. Since this suppression sound may be softer than the tinnitus, the total sound environment may be decreased by use of the present invention.

Figure 2:
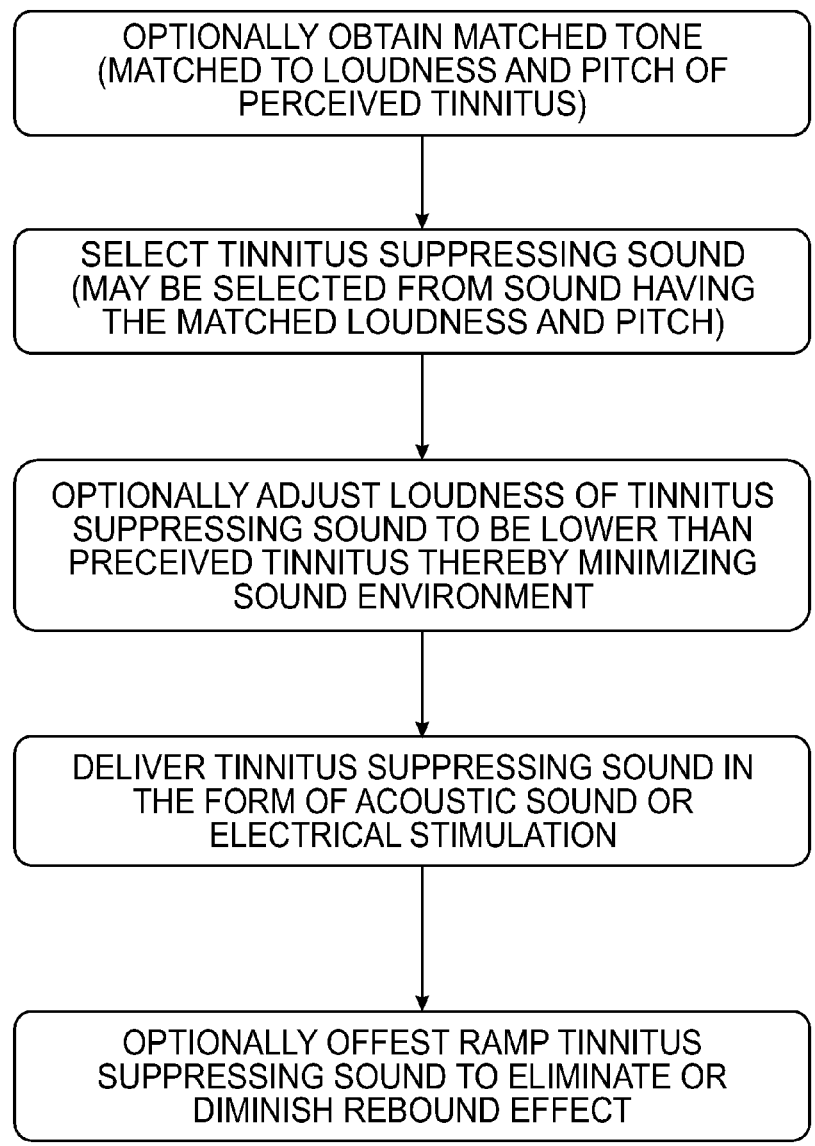
FIG. 2 is a flow diagram showing an example of a method of the present invention.

FIG. 2 shows a flow diagram of one example of a tinnitus suppressing method of the present invention. In this method, a matched tone may optionally be obtained for loudness and pitch of the subjective tinnitus. Such tinnitus matching tone is obtained by presenting an external tone to the subject who is instructed to adjust the tone's amplitude and frequency to match the perceived tinnitus' loudness and pitch. The external tone is optimally presented to the ear contralateral to the tinnitus ear if the tinnitus is unilateral, or to the ear with the least amount of hearing loss if the tinnitus is bilateral. Additionally, the tinnitus matching tone is the most accurately obtained by a double-bracketing procedure in which the amplitude of the external tone is first presented to be much softer than the perceived tinnitus loudness and then to be much louder; the range of the softer and louder amplitudes is reduced until the external tone is just noticeably softer or louder than the perceived tinnitus loudness. The average of the just noticeable softer and louder amplitudes for the external tone is the matched tinnitus loudness. Once the matched tinnitus loudness is obtained, the frequency of the external tone is varied to be much lower and higher than the perceived tinnitus pitch. Similarly, the range of the frequencies is reduced until the external tone is just noticeably lower or higher than the perceived tinnitus pitch. The average of the noticeable lower and higher frequencies for the external tone is the matched tinnitus pitch.

Second, a tinnitus suppressing sound (which may have the matched loudness and pitch) is selected for use with the subject. This may be accomplished in any suitable way. For example, the subject may listen to a series of sounds (e.g., through headphones) and select the particular sound that he or she perceives to be the same as or highly similar to the perceived tinnitus. That selected sound may then be used as the tinnitus suppressing sound. Another example would be to utilize a pre-selected tinnitus suppressing sound that has been determined by prior experience to suppress tinnitus in a substantial number of subjects. The tinnitus suppressing sound may be amplitude or frequency modulated sound.

After the tinnitus suppressing sound has been selected, it is delivered to the subject in a series of treatments or continuously to effect suppression of the subject's tinnitus. As described more fully below, the tinnitus suppressing sound may delivered in the form of acoustic sound (e.g., via speakers, earphones, headset, earbuds, ear canal inserted speakers, etc.) or as electrical stimulation to the cochlea, auditory nerve or appropriate area of the brain. Non-limiting examples of cochlear implants and implantable electrodes that may be used to deliver tinnitus suppressing treatments of the present invention are described in the above-incorporated United States Patent Application Publication 2007/0203536 (Hochmair et al.).

Optionally, the tinnitus suppressing sound or at least one component or variable of the tinnitus suppressing sound may be varied to optimize the degree to which the subject's tinnitus is suppressed.

Also, optionally, the loudness of the tinnitus suppressing sound may be adjusted to be softer than the tinnitus, thereby allowing the subject to avoid being subjected to an unnecessarily high perceived sound environment. The tinnitus suppressing sound may be delivered as acoustic sound or as electrical stimulus, such as electrical stimuli delivered via a cochlear implant.

Also, optionally, when it is desired to terminate the tinnitus suppressing sound (such as at the end of a particular treatment period) the sound may be gradually turned off, producing an offset ramp that decreases the loudness of the tinnitus suppressing sound to eliminate a sudden rebound of the tinnitus.

Figure 2A:
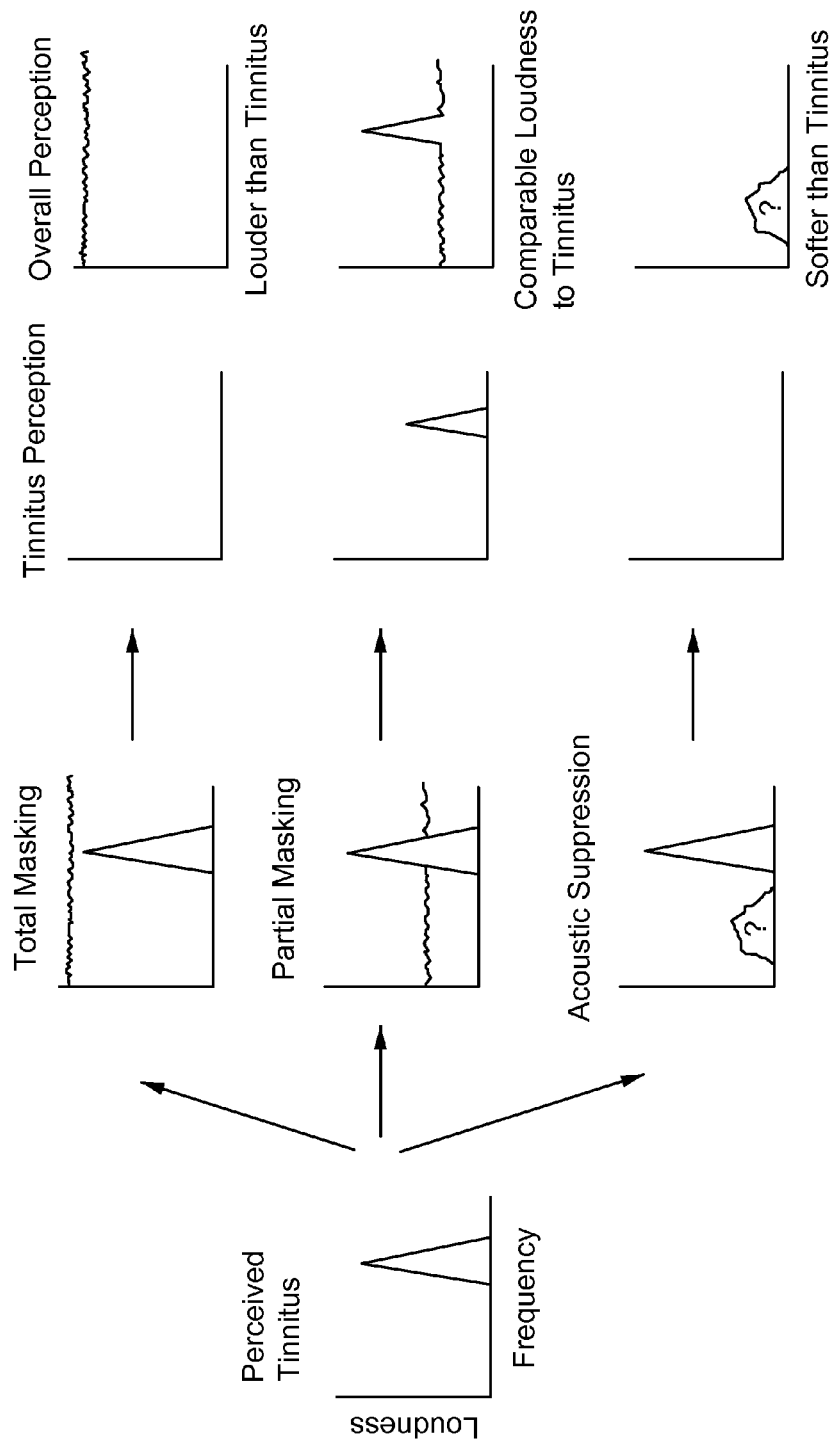
FIG. 2A is a graphic illustration showing differences between tinnitus masking and tinnitus suppression.

FIG. 2A shows graphically the differences between tinnitus masking and tinnitus suppression. With total masking, the tinnitus will not be audible, but the masker will be louder than the tinnitus. For partial masking, the masker is softer than the tinnitus, the perception of the tinnitus is reduced, but the overall level of sound (masker plus tinnitus) is similar to the tinnitus alone. For suppression, a sound is presented that is softer than the tinnitus but completely eliminates the perception of the tinnitus. The overall level will be less than the tinnitus alone.

The present invention includes a sound delivery device and method to suppress tinnitus. The device is any device that is usable to deliver sound that has complementary characteristics to the tinnitus. Such sound may be delivered acoustically via an audio device (e.g., stereo or mono sound emitting device with speaker(s) (e.g., speakers, earpiece(s), headphone(s), etc.) or electrically via an electrode or electrode array, such as a needle electrode, ear implant, cochlear implant, etc. The sound can be static or dynamic, including pure tones, click trains, amplitude-modulated and frequency-modulated sounds as well as speech and music. The sound will typically include a long offset ramp to reduce or eliminate the rebound of tinnitus after the suppression. A rebound is defined as an increase in the perceived level of tinnitus following a sound that masks or suppresses it.

Further in accordance with the present invention, there are provided devices and methods which provide to a subject's brain sound input that is complementary to tinnitus, thereby suppressing the tinnitus. One advantage of the present invention is that it may provide an external sound that doesn't have to be as loud as the perceived tinnitus sound, and in fact, can be much softer than the perceived tinnitus sound or barely audible, but can nonetheless suppress tinnitus. The search for such suppressor sound can be optimized with a biofeedback processor.

One objective of the present invention is to deliver an effective and low-cost means of completely suppressing tinnitus via custom and patterned acoustic or electric stimulation. Applicant's approach is to identify these customized and patterned acoustic and electric stimuli in a selected group of patients whose tinnitus cannot be controlled by current conventional methods. Although the mechanisms are unclear, it is hypothesized that a unique external stimulus, acoustic or electric, exists to suppress tinnitus for each patient. Based on Applicant's data, this unique stimulus is able to suppress tinnitus effectively and to operate in a totally different mechanism than masking. For the traditional masker to be effective, it needs to have similar temporal and spectral properties to the tinnitus. For the present suppressor, it tends to have complementary properties to the tinnitus, e.g., a low-pitch sound can be used to suppress high-pitched tinnitus.

A further objective of the present invention is to provide additional means for studying and elucidating the mechanisms underlying tinnitus and tinnitus suppression as well as to identify an objective marker of tinnitus.

EXAMPLE 1

Figure 1:
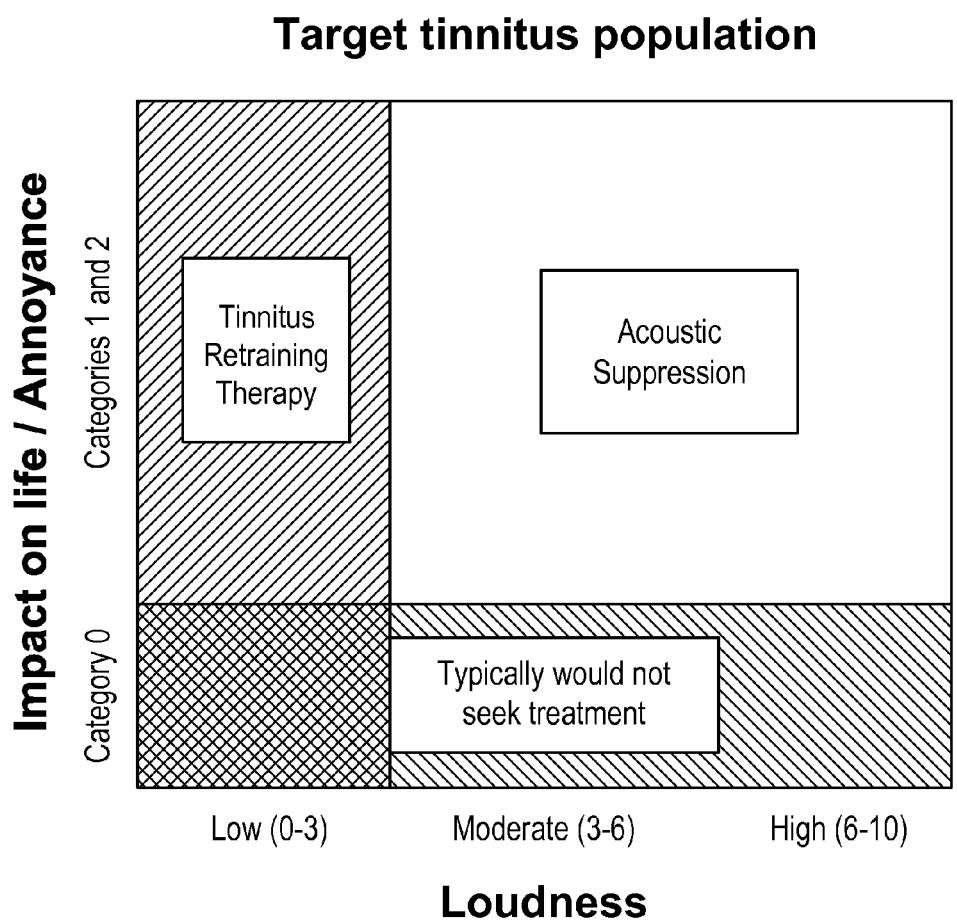
FIG. 1 is a graphic representation of tinnitus severity classifications and a typical tinnitus patient population.

In this example, two adults with unilateral continuously high-level tinnitus were identified and tested. Subject AS1 has had tinnitus for 2.5 years, a moderate loss of 50 dB at 8 kHz, ranks the tinnitus to be 7 of 10 loud, and matches the tinnitus to an 8-kHz, 70-dB SPL pure tone in the contralateral ear. AS1 is thus a Category 1 unilateral High (see FIG. 1). Subject AS2 has had tinnitus for 1.5 years, a hearing loss of 25-40 dB at 4-8 kHz, ranks the tinnitus to be 5 of 10, and matches the tinnitus to a 7-kHz, 69-dB SPL pure tone in the contralateral ear. AS2 is a Category 1 unilateral Moderate.

Figure 3:
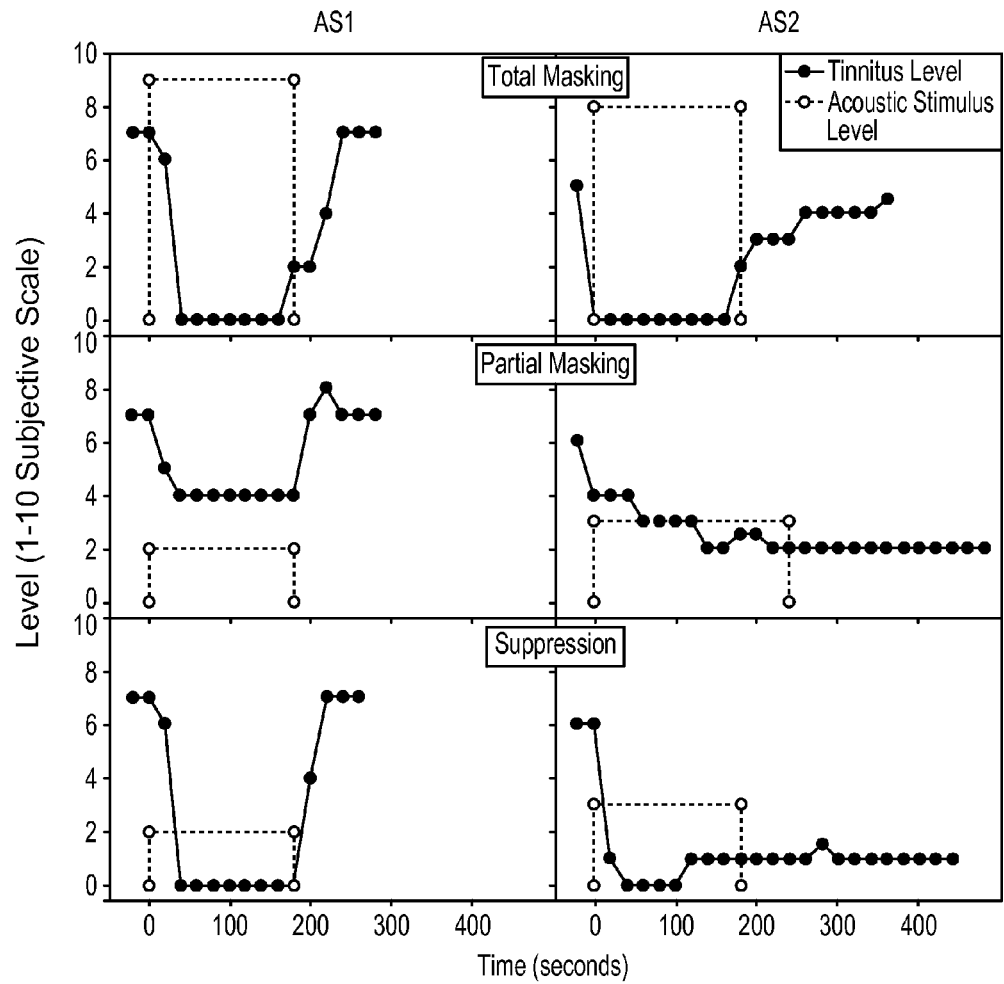
FIG. 3 is a composite graph of loudness level vs. time duration which estimates loudness for both tinnitus and the external sound as a function of the sound duration in each of two subjects treated in Example 1 below.

FIG. 3 shows loudness estimate for both tinnitus and the external sound as a function of the sound duration. An 8-kHz tone presented at 80 dB SPL can totally mask AS1's tinnitus (upper left panel). An 8-kHz tone presented at 60 dB SPL can partially mask the tinnitus from 7 to 4 loud (middle left panel). However, the same tone presented 60 dB SPL (2 loud), if amplitude-modulated by an 80-Hz sinusoid, can totally suppress the tinnitus (bottom left panel). Subject AS2 showed a similar pattern except for significant residual suppression lasting up to 30 minutes.

Figure 4:
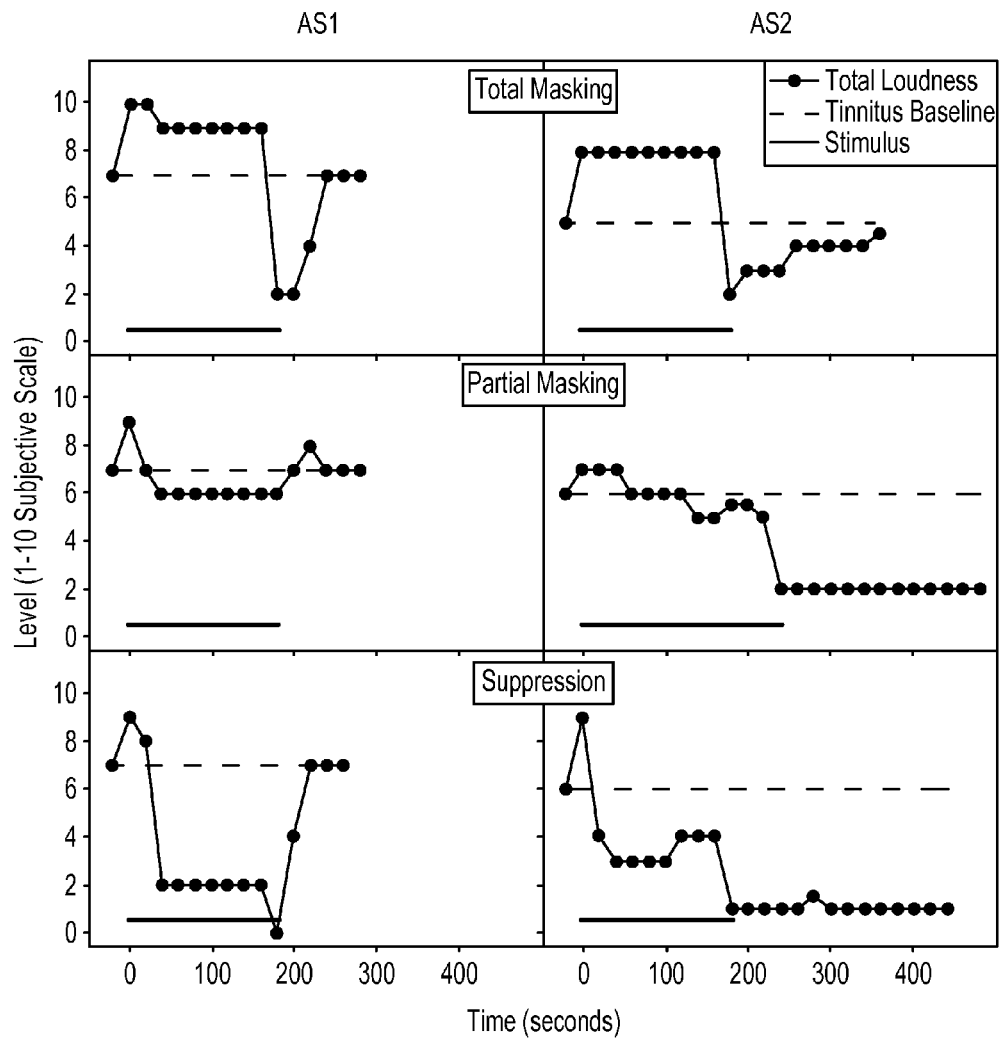
FIG. 4 is a composite graph of loudness level vs. time duration which estimates the total loudness of the tinnitus and the tinnitus suppressing or masking sounds in order to compare the effectiveness of masking versus suppression in each of two subjects treated in Example 1 below.

FIG. 4 estimates the total loudness of the tinnitus and the sound in order to compare the effectiveness of masking versus suppression. The dashed line represents the initial level of tinnitus and is used to show if the overall percept is higher or lower. In total masking, the perception is higher during the presentation of the stimulus due to the fact that the sound needed to be louder than the tinnitus. For partial masking, the overall level is roughly equal to the tinnitus during the presentation. Subject AS2 had lower sound after offset due to extraordinary residual inhibition. With suppression, the overall level is decreased during the presentation of the sound. The bottom line is that suppression can be a viable treatment to reduce the subject's overall perceived loudness of the tinnitus and the external sound. In other words, we can replace tinnitus with a much softer, and hopefully much more pleasant, external sound. Ideally we would like to find an external stimulus that is sub-threshold or can totally adapt while still effective in totally suppressing tinnitus. At present, the 80-Hz amplitude modulated sound represents the best option for AS1 who has purchased an Ipod and downloaded an 8-hour version of this modulated sound to relieve his tinnitus on a daily basis.

In this example, a 47-year-old male subject, who has had unilateral hearing loss (right ear), imbalance and debilitating tinnitus since June 2004. He received a Clarion HiRes 90K cochlear implant device (in his right ear to control tinnitus. The subject had reported no relief from the HiRes Sequential strategy loaded in the Auria processor. Tinnitus quality was measured by matching between the tinnitus in the right ear and the sound delivered to his good ear (normal hearing in the left ear), and mainly consisted of band-passed noise from 500-8000 Hz at 70-90 dB SPL with intermittent higher frequency components. He is a Category 2 unilateral High.

To test the effect seen in prior art, this subject was stimulated with 5000 Hz pulse trains. Apical and basal as well as monopolar and bipolar configurations were tested. Pulse widths were 53.9 us/phase. Monopolar stimulation is delivered using one intracochlear electrode and one reference electrode (Clarion HiRes 90K cochlear implant, Advanced Bionics, Valencia, Calif.) located on the internal receiver of the cochlear implant device, which indicates that the current will have a broad stimulation area. Bipolar stimulation is delivered using two adjacent intracochlear electrodes, which indicates that the region of stimulation will be much more restricted. A research interface and software (Bionic Ear Data Collection System—BEDCS, Advance Bionics Corp., Valencia, Calif.) were used to generate and deliver the electric stimulation.

Figure 5:
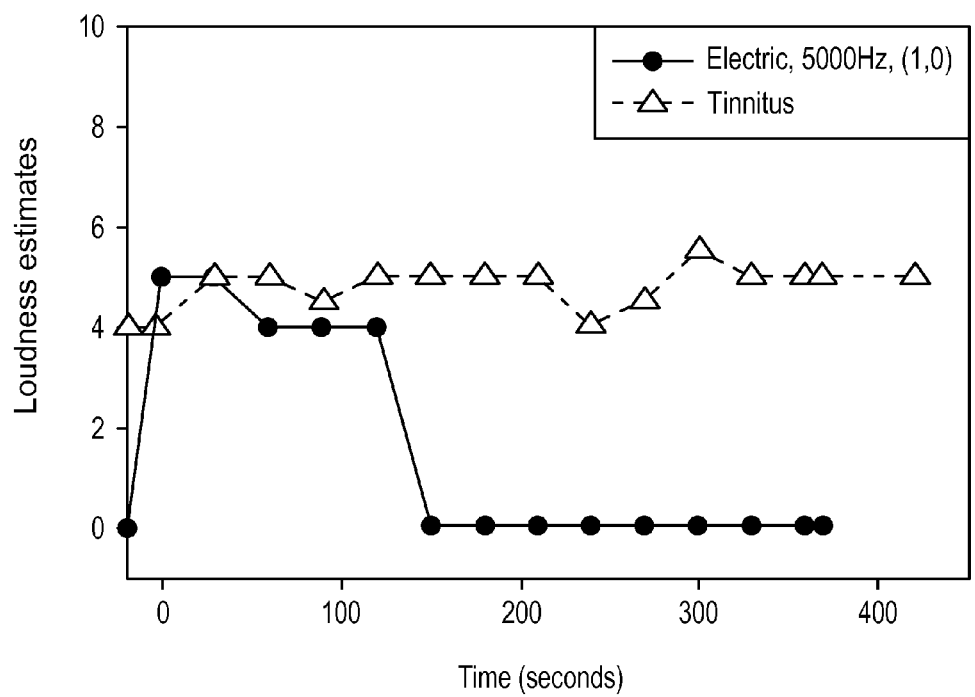
FIG. 5 is a graph of loudness estimates vs. time showing the monopolar apical condition and demonstrating that while the stimulus produced total adaptation, no effect was seen on the tinnitus in one of the subjects treated in Example 1 below.

FIG. 5 shows the monopolar apical condition and demonstrates that while the stimulus produced total adaptation, no effect was seen on the tinnitus in this subject. Loudness adaptation was measured using the successive loudness estimation every 30 seconds (See Tang, Liu and Zeng JARO 2006). Similar results were seen with all high rate stimulation.

Figure 6:
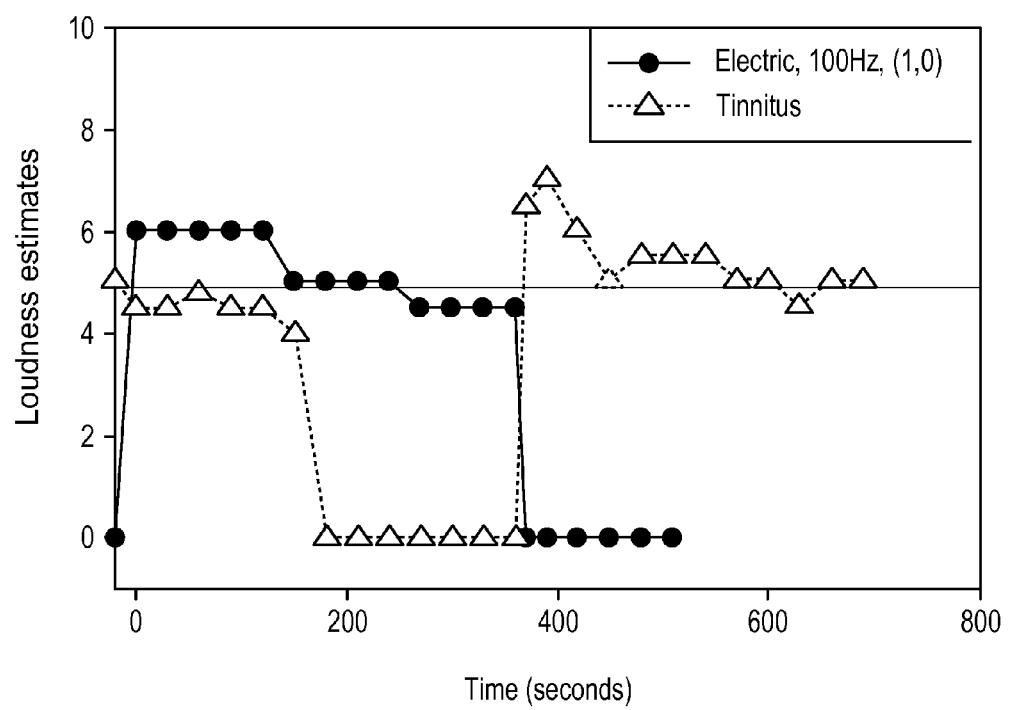
FIG. 6 shows that low-rate stimulation (100 Hz) produced little or no adaptation but could totally suppress his tinnitus.

On the other hand, FIG. 6 shows that low-rate stimulation (100 Hz) produced little or no adaptation but could totally suppress his tinnitus. A 40% increase ("rebound") above baseline tinnitus was observed at the offset of the electric stimulus and lasted for about 1 minute.

Applicants have also found that the effective suppressor required critical rates (20-130 Hz), critical places (the most apical several electrodes), and critical level (had to be at least 2 of 10 loud). Pulse width for the effective low rate stimuli were 107.8 us/phase. Objective measures in both spontaneous and event-related evoked potentials also showed a difference related to the presence and absence of tinnitus.

Applicants have since produced a similar sound using his clinical speech processor that also resulted in effective tinnitus suppression. The patient has used this modified processor on a daily basis to relieve his tinnitus. As a result, this patient has stopped taking medication for his tinnitus.

These data show a fundamental difference between suppression and masking. Ideally the promising results can be generalized to a wide range of patients.

Test Stimuli

For acoustic suppression, sound was generated digitally using the Tucker-Davis Technologies (TDT) system III (Tucker-Davis Technologies, Inc., Alachua, Fla.) and delivered through headphones. A 16-bit D/A converter will be used with a 44,100 Hz sampling rate. A 2.5-ms ramp will be applied to all stimuli to avoid spectral splatter. Stimuli will include pure tones from 20 Hz to 10 kHz, sinusoidal amplitude modulated (SAM) tones with center frequencies 100 Hz to 10 kHz and modulation frequencies from 0.5 Hz to a 25% of the center frequency, and band pass noises at different cutoff frequencies. Levels from barely audible to sufficiently loud to completely mask will be used.

Subjects with cochlear implants will have their internal receiver connected directly to the research interface bypassing their external speech processor. Electric stimulation will be delivered either as pulse trains or as electric sinusoids where possible (e.g., Bionic Ear Data Collection System—BEDCS, Advanced Bionics, Valencia, Calif.). Stimulation rates from 10 to 10,000 pps, all electrodes from apex to base, and envelope modulation rates from 0.5 Hz to 25% of the carrier pulse rate will be tested. Levels consistent with the acoustic stimuli will be used. Stimuli are verified through an oscilloscope to confirm accuracy before delivery to the subjects.

Test Procedure

If the subject has normal or some degree of residual hearing, tinnitus will be matched to external stimuli in terms of the loudness and pitch. This is done by presenting a low pitch (100 Hz) or a high pitch (10000 Hz) to the contralateral ear in unilateral tinnitus or the ear with softer tinnitus in bilateral tinnitus. The subject is asked to identify the pitch as higher or as lower than their tinnitus. The frequency is adjusted until it is deemed a match or very close. If the sound quality is too different from a pure tone to warrant a match, the subject is asked to describe the sound and another match using broad or narrow band noise or an amplitude or frequency modulation will be attempted. Level is then adjusted to match the loudness between tinnitus and the external stimulus. Should accurate match be needed, the PI has developed and used a double-staircase adaptive procedure (Zeng and Turner 1991).

The subjects are instructed to be familiar with a 1-10 ranking scale with 1 being threshold, 6 being most comfortable level (MCL), and 10 being the upper limit of loudness (ULL). Subjects report the level of their tinnitus prior to any acoustic or electric presentation. The stimuli are presented and the subject is asked to report on the loudness of the presented sound and the level of their tinnitus at 20-second intervals. Subjects will be instructed to try to make independent reports of loudness that are not biases by previous responses. If the subject cannot identify their tinnitus in the presence of the stimulus, a value of zero will be assigned. Sounds will be presented for 3 to 6 minutes. Reports are made for 1 to 4 minutes after stimulus offset to measure the presence and duration of residual inhibition.

Potential Problems and Alternative Strategies

In at least some subjects, a rebound increase in tinnitus can occur after the offset of an acoustic or electric tinnitus suppressing sound in this invention. In some cases, the rebound can persist for hours when a suppressor is used upwards of 8 hours. One method to alleviate the rebound is to produce an offset ramp of approximately one minute in the suppressor. The offset ramp gradually decreases the amplitude of the tinnitus suppressing sound over a 1 minute or longer period.

The above-described event-related evoked potentials can be used to derive a tinnitus "signature" that can then be used to objectively identify the presence and absence of tinnitus. Applicants have found that N100 may be such a signature. Identification of an objective tinnitus signature is critical to the assessment of the effectiveness of tinnitus treatment as well as the diagnosis of tinnitus in children and the development of an animal tinnitus model.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless otherwise specified of if to do so would render the embodiment or example unsuitable for its intended use. Also, where the steps of a method or process have been described or listed in a particular order, the order of such steps may be changed unless otherwise specified or unless doing so would render the method or process unworkable for its intended purpose. All reasonable additions, deletions, modifications and alterations are to be considered equivalents of the described examples and embodiments and are to be included within the scope of the following claims.

What is claimed is:

1. A method for generating a modulated sound for treating tinnitus in a human subject, comprising the steps of:
adjusting a frequency of a presented sound as a function of feedback from a human subject to generate an adjusted sound comprising at least a matched pitch of the subject's tinnitus;
generating a sound comprising the matched pitch; and
amplitude modulating or frequency modulating the generated sound to generate a modulated sound, wherein the modulated sound has an adjustable intensity lower than the subject's perceived loudness of the tinnitus.

2. The method of claim 1, wherein the adjusting step comprises adjusting the frequency of the presented sound including reducing a range of frequencies until the matched pitch is reached, wherein said range of frequencies varies from lesser than to greater than a perceived pitch.

3. The method of claim 1, wherein the adjusting step comprises adjusting an amplitude of the presented sound.

4. The method of claim 3, wherein the adjusting step comprises adjusting the amplitude of the presented sound including reducing a range of amplitudes until a perceived loudness is reached, wherein said range of amplitudes varies from zero to greater than a perceived loudness.

5. The method of claim 1, further comprising applying the modulated sound to the subject, thereby suppressing the tinnitus of the subject.

6. The method of claim 5, further comprising receiving additional feedback from the subject after applying the modulated sound and, as a function of the additional feedback, adjusting an intensity of the modulated sound within a range from zero to less than a perceived loudness.

7. The method of claim 1, further comprising adding an offset ramp to the modulated sound.

8. The method of claim 1, further comprising storing the modulated sound to a portable audio device.

9. The method of claim 1, wherein the modulating step comprises modulating the generated sound with a sinusoid to generate the modulated sound.

10. The method of claim 1, wherein the generated sound has an amplitude and wherein the modulating step comprises modulating the amplitude of the generated sound to generate an amplitude-modulated sound.

11. The method of claim 1, wherein the generated sound has a frequency and wherein the modulating step comprises modulating the frequency of the generated sound to generate a frequency-modulated sound.

12. A device for generating a modulated sound for treating tinnitus in a human subject, said device comprising:
a processor executing instructions for:
adjusting a frequency of a sound presented to a human subject as a function of feedback received from a subject to generate an adjusted sound comprising a matched pitch of the subject's tinnitus;
generating a sound comprising the matched pitch; and
amplitude modulating or frequency modulating the generated sound to generate a modulated sound, wherein the modulated sound has an adjustable intensity lower than the subject's perceived loudness of the tinnitus.

13. The device of claim 12, the processor further executing instructions for applying the modulated sound to the subject via an audio interface, thereby suppressing the tinnitus of the subject.

14. The device of claim 12, wherein the processor further executes instructions for:
presenting the sound to the subject via an audio interface; and
receiving the feedback from the subject via an input interface.

15. The device of claim 14, further comprising:
the audio interface for presenting the sound to the subject; and
the input interface for receiving the feedback from the subject.

16. The device of claim 15, the processor further executing instructions for applying the modulated sound to the subject via the audio interface, thereby suppressing the tinnitus of the subject.

17. The device of claim 12, wherein said adjusting further includes adjusting an intensity of the presented sound.

18. The device of claim 12, the processor further executing instructions for:
receiving additional feedback from the subject after applying the modulated sound; and,
as a function of the additional feedback, adjusting an intensity of the modulated sound within a range from zero to less than the perceived loudness.

19. The device of claim 12, wherein the processor further executes instructions for transferring the modulated sound to a portable audio device.

20. The device of claim 12, wherein the device includes a portable audio device.

21. The device of claim 20, wherein the portable audio device comprises an acoustic ear device, an earpiece, a headset or a speaker for producing a sound as a function of the modulated sound.

22. The device of claim 12, wherein the generated sound is modulated with a sinusoid to generate the modulated sound.

23. The device of claim 12, wherein the generated sound has an amplitude and wherein the modulating step comprises modulating the amplitude of the generated sound to generate an amplitude-modulated sound.

24. The device of claim 12, wherein the generated sound has a frequency and wherein the modulating step comprises modulating the frequency of the generated sound to generate a frequency-modulated sound.

* * * * *